United States Patent [19]

Frantzen et al.

[11] Patent Number: 5,739,318
[45] Date of Patent: Apr. 14, 1998

[54] LABELLING AGENTS COMPRISING BORONIC ACID CONJUGATES

[75] Inventors: Frank Frantzen, Tverlandet; Erling Sundrehagen, Oslo, both of Norway

[73] Assignee: Axis Research AS, Oslo, Norway

[21] Appl. No.: 50,275

[22] PCT Filed: Nov. 13, 1991

[86] PCT No.: PCT/EP91/02160

§ 371 Date: Jul. 12, 1993

§ 102(e) Date: Jul. 12, 1993

[87] PCT Pub. No.: WO92/08722

PCT Pub. Date: May 29, 1992

[30] Foreign Application Priority Data

Nov. 14, 1990 [GB] United Kingdom ............ 9024775

[51] Int. Cl.[6] .................... C09B 47/04; C09B 62/00; C09B 67/00
[52] U.S. Cl. .................... 540/128; 540/122; 540/131; 540/132; 540/139; 540/140; 544/102; 544/103; 544/106; 544/109; 544/110; 562/7
[58] Field of Search .................... 562/7; 544/101, 544/102, 103, 106, 109, 110; 540/122, 128, 131, 132, 139, 140

[56] References Cited

U.S. PATENT DOCUMENTS

| 4,496,722 | 1/1985 | Gallop et al. | 544/69 |
| 4,830,786 | 5/1989 | Pease et al. | 552/302 |
| 4,861,728 | 8/1989 | Wagner | 436/501 |
| 5,242,842 | 9/1993 | Sundrehagen | 436/536 |

FOREIGN PATENT DOCUMENTS

| 0 310 361 | 4/1989 | European Pat. Off. . |
| 0 319 620 | 6/1989 | European Pat. Off. . |
| 0 455 225 | 11/1991 | European Pat. Off. . |
| 3 720 736 | 1/1989 | Germany . |
| A-2-226070 | 10/1990 | Japan . |
| WO 90 13813 | 11/1990 | WIPO . |

OTHER PUBLICATIONS

Fabian et al., "Light Absorption of Organic Colorants," Springer-Verlag, 1980, p. 157.
Koyama, *Chemical Abstracts*, 114:118100h, 1990.

*Primary Examiner*—Marianne M. Cintins
*Assistant Examiner*—Dwayne C. Jones
*Attorney, Agent, or Firm*—Bacon & Thomas

[57] ABSTRACT

The present invention relates to labelling agents comprising non-proteinaceous boronic acid conjugates having absorption maxima at not less than 600 nm, said label being provided by e.g., an azine, triphenylmethane, cyanine or phthalocyanine dye. The labelling agents are useful in the estimation and quantification of cisdiols such as glycosylated haemoglobin, by virtue of the substantially total absence of overlap with the absorption spectrum of haemoglobin. Oxazine and thiazine dyes exhibiting similar absorption characteristics and containing other activated moieties are similarly useful labelling agents, especially in the presence of haemoglobin.

5 Claims, No Drawings

LABELLING AGENTS COMPRISING BORONIC ACID CONJUGATES

This case is a 371 of PCT/EP91/02160, filed on Nov. 13, 1991.

BACKGROUND OF THE INVENTION

1. Field of the Invention

This invention relates to novel compounds useful as labelling agents, more particularly to novel dyes exhibiting absorption maxima at or beyond the red extreme of the visible spectrum.

2. Description of the Prior Art

Labelling agents are frequently required in studies of blood samples, e.g. in measurements of glycosylated haemoglobin as part of an evaluation of blood glucose levels in patients suffering from diabetes mellitus. Such agents are described in, for example, DE-A-3720736 and U.S. Pat. No. 4,861,728 and typically comprise a boronic acid reagent which is capable of reacting with the cis-diol grouping of the glycosyl moiety and which is bonded to a fluorescent and/or coloured dye, e.g. a diazo conjugate or fluorescein, rhodamine or phycobiliprotein. Assessment of quantification of the fluorescence or absorbance, e.g. by reflectometry, affords a measure of the glycosylated haemoglobin levels in the blood samples.

A disadvantage of the use of phycobiliprotein conjugates of boronic acids is that in most glycosylated haemoglobins the glycosyl moiety, which is principally attached to the N-terminal valine amino acid of the beta-chain, is effectively located in a narrow "pocket" of the haemoglobin molecule and is therefore not readily accessible to high molecular weight reagents.

Other previously proposed coloured labels such as fluorescein and rhodamine suffer the disadvantage that their absorption spectra overlap significantly with the absorption spectrum of haemoglobin; this can prevent or seriously inhibit effective spectroscopic quantification of the label.

SUMMARY OF THE INVENTION

The present invention is based on our discovery of new classes of labelling compounds which exhibit an absorption maximum at not less than 600 nm, at which wavelengths haemoglobin has minimal absorption.

According to one aspect of the invention we provide non-proteinaceous boronic acid conjugate compounds having absorption maxima at not less than 600 nm. Such compounds may, for example, be represented by the formula (I)

wherein V is a chromophoric and/or fluorophoric moiety exhibiting an absorption and/or emission maximum at not less than 600 nm and W is a linking organic group.

It will be appreciated that the dihydroxyboryl residue may also exist in the anionic form

depending on the pH and electrolyte content of reagent compositions employed and that such compounds are to be regarded as within the scope of formula (I).

The boronic acid conjugates of the invention are useful in spectroscopic studies relating to estimation or quantification of cis-diols, particularly of glycosylated moieties, e.g. proteins, in the presence of haemoglobin since there is virtually no overlap between the absorption spectra of haemoglobin and the chromophore.

DESCRIPTION OF THE PREFERRED EMBODIMENTS

The boron atom of the boronic acid residue is advantageously attached to a phenyl group, e.g. an aminophenyl group, such as a m-aminophenyl group. Depending on the pKa value desired for the boronic acid, the phenyl group may optionally be further substituted, e.g. by one or more substituents which influence the pKa value without sterically interfering with bonding between the boronic acid residue and the target cis-diol. Examples of electron-withdrawing substituents which may be employed to enhance the degree of ionisation and thus the association constant of the boronic acid to target cis-diols such as glycosylated moieties include nitro, lower alkoxy such as methoxy or ethoxy, and acyl groups such as formyl or lower alkanoyl. Representative boronic acids of this type include 2-nitro-5-aminophenyl boronic acid and the corresponding 3-nitro and 4-nitro isomers. In general any such phenyl or substituted phenyl groups may be linked directly to the chromophoric and/or fluorophoric moiety V, so that the phenyl group constitutes the group W in formula (I), or via linking or spacing groups, e.g. as known in the art.

One useful category of compounds according to the invention comprises compounds of formula (II)

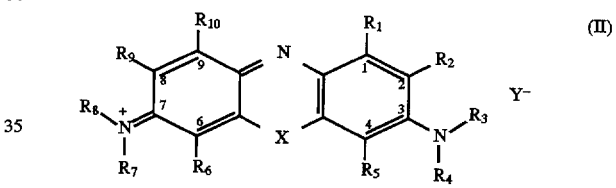

wherein X represents an oxygen or sulphur atom;

$Y^-$ represents an anion (e.g. a halide ion such as chloride or bromide, or a perhaloate ion such as perchlorate); and $R_1$-$R_{10}$ are each selected from hydrogen atoms and organic groups, or $R_1$ and $R_2$ and/or $R_9$ and $R_{10}$ may, together with the carbon atoms to which they are attached, form a fused monocyclic or polycyclic ring system, with the provisos that at least one of $R_3$ and $R_4$ and at least one of $R_7$ and $R_8$ are other than hydrogen and that at least one of $R_1$-$R_{10}$ is an organic group containing a boronic acid residue.

Where any of $R_1$-$R_{10}$ represent organic groups these may, for example, be selected from alkyl, alkenyl and alkynyl groups, e.g. containing up to 6 carbon atoms, such as methyl, ethyl, n-propyl, isopropyl, n-butyl, sec-butyl, t-butyl, vinyl, allyl, ethynyl or propargyl; cycloalkyl or cycloalkenyl, e.g. containing 5-7 carbon atoms, such as cyclopentyl, cyclohexyl, cycloheptyl, cyclohexenyl or cyclopentadienyl; aryl groups, e.g. containing 6-12 carbon atoms, such as phenyl, tolyl or naphthyl; heterocyclic rings, e.g. 5-7 membered saturated and unsaturated rings containing at least one heteroatom selected from oxygen, nitrogen and sulphur, such as furyl, thienyl, pyridyl, pyrimidyl, pyridazyl, thiazolyl, thiazinyl, triazinyl, pyrrolyl, imidazolyl, pyrazolyl, pyrrolidinyl, piperidinyl, piperazinyl or morpholinyl; lower (e.g. $C_{1-4}$) alkyl substituted by any of the previously described cycloalkyl, cycloalkenyl, aryl or heterocyclic groups; any of the previous groups interrupted and/or substituted by one or more heteroatoms, e.g. so as to contain one or more ether, thioether, amino, amido, carbonyl or thiocarbonyl groups; or any of the previous groups carrying one or more substituents which may, for example, be selected from hydroxy, mercapto, amino, halo, nitro, azido, carboxy, cyano and isothiocyanato, or any other substituent compatible with the boronic acid residue.

Indeed in general in the compounds of the invention, unless otherwise specified, alkyl, alkenyl and alkenylene moieties will contain up to 6 carbon atoms and cyclic groups will have 5 to 7 membered rings.

One useful group of compounds embraced by formula (II), by virtue of their hydrophilic properties, are compounds of formula (III)

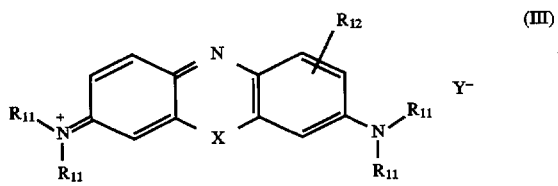

(wherein X and Y⁻ are as hereinbefore defined; each $R_{11}$ independently is a lower (e.g. $C_{1-6}$) alkyl group such as methyl or ethyl; and $R_{12}$ is an organic group containing a boronic acid residue). It will be appreciated that, in view of the symmetry of the resonance-stabilised ring system, $R_{12}$ substituents at the 1-, 2- and 4- positions are equivalent to corresponding substituents at the 9-, 8- and 6- positions respectively.

Examples of $R_{12}$ groups which may be present in such compounds (III) include the following:

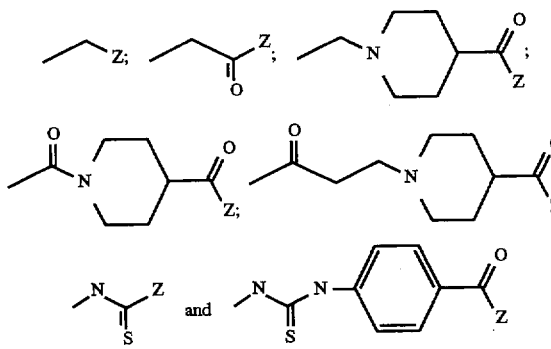

where Z represents a group containing a boronic acid residue, e.g. an aminophenyl boronic acid residue such as the group

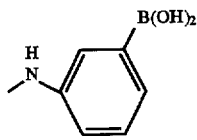

A further useful class of hydrophilic compounds (II) may be represented by formula (IV)

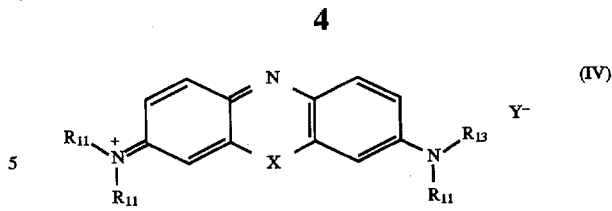

(wherein X, Y⁻, and $R_{11}$ are as hereinbefore defined and $R_{13}$ is an organic group containing a boronic residue, e.g. as hereinbefore described). It will again be appreciated that the organic group containing the boronic acid residue has identical effect whether shown as a substituent of the 3- amino or the 7-imino grouping.

Examples of organic groups containing a boronic acid residue which may be present in such compounds (IV) include

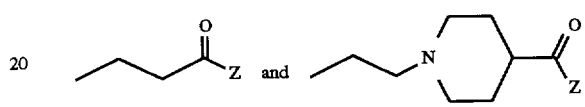

wherein Z is as hereinbefore defined.

Another useful category of compounds according to the invention includes those in which V is derived from a triphenylmethane dye, e.g. as represented by formula (V)

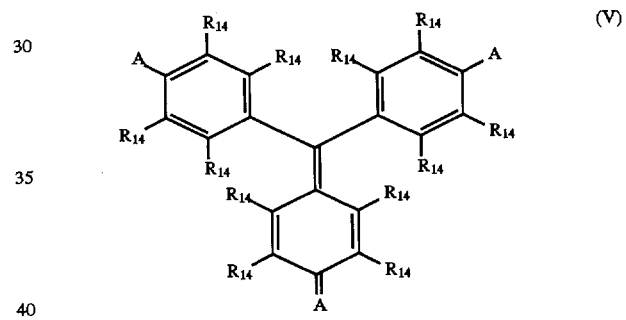

in which each $R_{14}$ independently represents a hydrogen atom, an organic group (e.g. as hereinbefore described in connection with $R_1$-$R_{10}$) or a (preferably hydrophilic) substituting group (e.g. hydroxy, carboxy, sulpho or chlorosulphonyl), and at least two of the A groups represent auxochrome groups, any non-auxochrome A group being as defined for $R_{14}$. Preferred auxochrome groups include amine/imine systems as represented by $N(R)_2/N^+(R)_2$ and NHR/N⁺HR systems (where each R represents an organic group, e.g. as hereinbefore described in connection with $R_1$-$R_{10}$, preferably a lower alkyl group such as methyl or ethyl), alone or in combination with O/OH. The —W—B(OH)₂ moiety may, for example, be attached to one of the phenyl rings, e.g. coupled via a group such as carboxy or sulpho, or to one of the R groups in an amine/imine auxochrome system. It will be appreciated that the other resonance structures which may be drawn are also intended to be within the scope of formula (V).

A further useful category of compounds according to the invention includes those in which V is derived from a phthalocyanine dye, e.g. as represented by formula (VI)

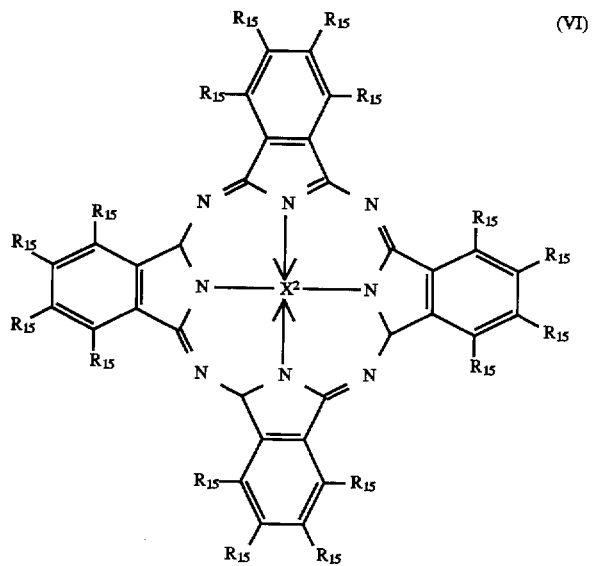

in which each $R_{15}$ independently represents a hydrogen atom, an organic group (e.g. as hereinbefore described in connection with $R_1$-$R_{10}$) or a (preferably water-solubilising) substituting group (e.g. carboxy, sulpho, chlorosulphonyl, hydroxy, phenoxy, or an amino group) and $X^2$ represents two hydrogen atoms or an atom of a "metallating" element (e.g. aluminium, cadmium, chromium, copper, gallium, germanium, magnesium, phosphorus, silicon, tin or zinc) which may, if of appropriate valency ($\geq 3$) carry one or more axial ligands (e.g. hydroxy or halo such as chloro).

A still further useful category of compounds according to the invention includes those in which V is derived from a cyanine or merocyanine dye, e.g. as represented by formulae (VII) and (VIII) respectively

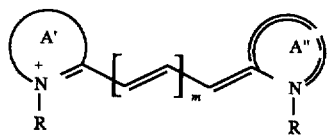

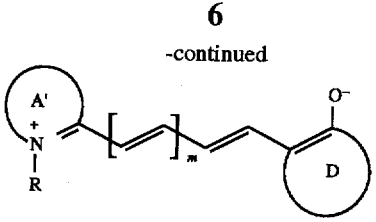

and the corresponding alternative resonance structures. In the above formulae A' and A" represent quaternised heteroatomic bases, D represents a ketomethylene-derived nucleus, R is as hereinbefore defined, and m is an integer, e.g. of 1–3, conveniently 2 or 3. Examples of dyes of this type include those of formula (IX)

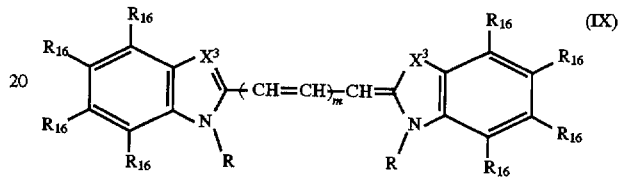

in which m and R are as hereinbefore defined, $X^3$ represents a heteroatom such as oxygen or sulphur or an optionally mono- or di-substituted methylene group, and each $R_{16}$ independently represents a hydrogen atom, an organic group (e.g. as hereinbefore described for $R_1$-$R_{10}$) or a (preferably water-solubilising) substituting group, or adjacent $R_{16}$ groups may together with the carbon atoms to which they are attached form fused monocyclic or polycyclic ring systems. Water-solubility enhancing substituents are desirably present as one or more of $R_{16}$, one preferred such substituent being carboxymethyl, which will conjugate to amine-containing molecules such as m-aminophenyl boronic acid with little or no change in the absorption characteristics of the cyanine chromophore.

A representative further class of azine dye conjugates according to the invention and a representative preparative sequence is illustrated in the following reaction scheme:

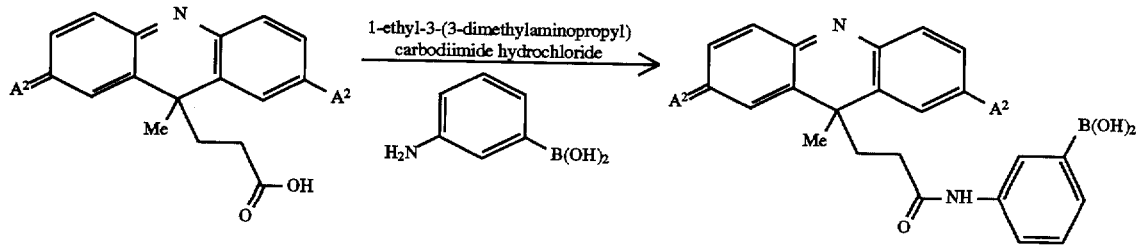

where each $A^2$ represents an $N(R)_2/N^+(R)_2$, $NHR/N^+HR$ or O/OH system as previously defined.

The boronic acid conjugates of the invention may be prepared according to the invention by reacting an appropriately functionalised dye having the required spectral characteristics with one or more reagents serving to introduce a boronic acid residue. Residues such as a phenyl boronic acid are conveniently synthesised from an aminophenyl boronic acid, preferably m-aminophenyl boronic acid, coupling to the rest of the molecule being effected by, for example, diazonium ion formation, silanisation or the use of a coupling agent (e.g. as taught in general chemical literature) such as a glutardialdehyde, carbodiimide, cyanogen halide or succinimide. Preferred aspects of the present process include (i) reaction of m-aminophenyl boronic acid with a carboxyl group-containing dye in the presence of a carbodiimide such as 1-ethyl-3-(3-dimethylaminopropyl) carbodiimide (EDC) to yield a compound (I) containing an amide-linked phenyl boronic acid group; (ii) activation of a carboxyl group-containing dye by the mixed anhydride method, for example by reaction with a haloformate ester (e.g. a lower alkyl haloformate such as isobutyl chloroformate), prior to reaction with m-aminophenyl boronic acid to yield an amide-linked phenyl boronic acid group; (iii) reaction of m-aminophenyl boronic acid with an isothiocyanato group-containing precursor to yield a compound (I) containing a thiourea-linked phenyl boronic acid group; and (iv) activation of a sulpho group-containing dye, for example by conversion to a sulphonyl halide such as the chloride, e.g. by reaction with a halogenating agent such as oxalyl chloride or phosphorus oxychloride, prior to reaction with m-aminophenyl boronic acid to yield a sulphonamide-linked boronic acid group.

Phenoxazine precursors for use in the preparation of compounds of formulae (II)–(IV) may, for example, be prepared by reaction sequences such as the following:

(A)
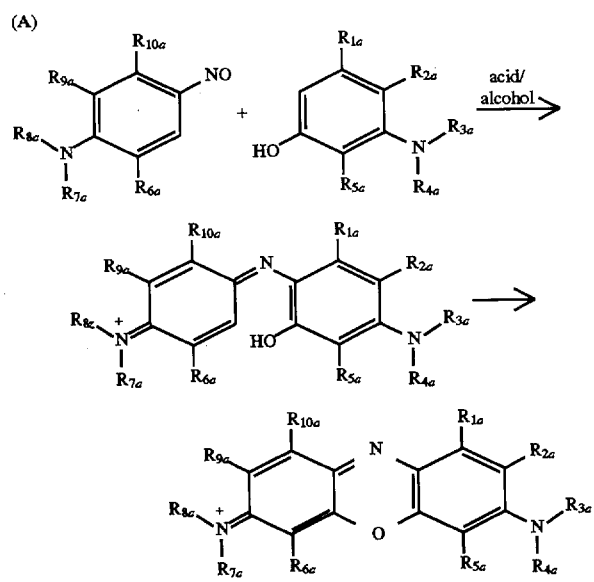

(B)
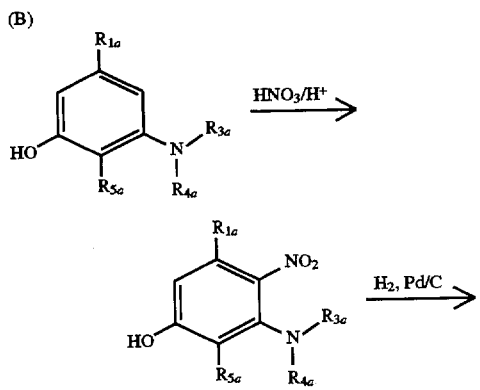

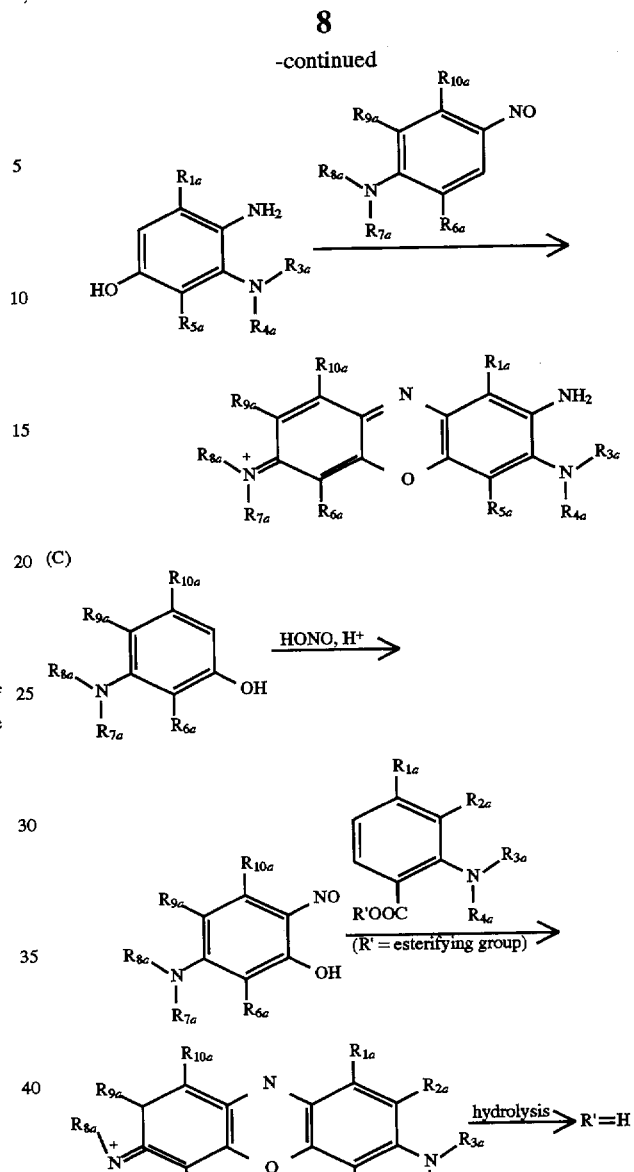

This scheme may be modified by interchanging the groups $R_{1a}$ and R'OOC to yield a 1- carboxy functionalised phenoxazine precursor.

-continued

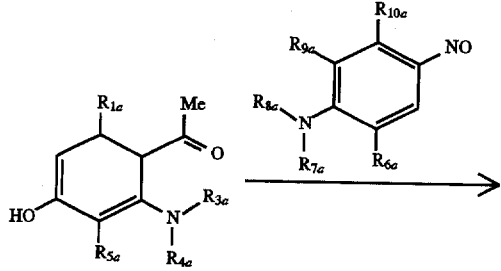

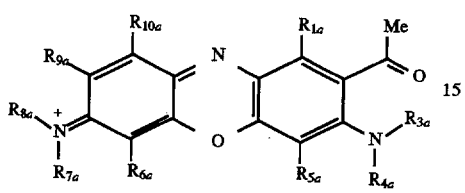

Alternatively, and preferably when all of $R_{3a}$, $R_{4a}$, $R_{7a}$ and $R_{8a}$ are other than hydrogen, a functionalised grouping (optionally incorporating a spacer group) may be attached to a carbon atom of the phenazine ring system by a Mannich-type synthesis, e.g. as shown in the following reaction scheme:

In the above schemes $R_{1a}$–$R_{10a}$ are as previously defined for $R_1$-$R_{10}$ except that they do not contain the boronic acid residue desired in the final product (II).

Phenothiazine precursors may be prepared by analogous techniques or using methods generally known in the art for the preparation of thiazine dyes.

Phenoxazine and phenothiazine precursors so obtained in which one of $R_{3a}$ and $R_{4a}$ or one of $R_{7a}$ and $R_{8a}$ is a hydrogen atom may be reacted with, for example, an alkyl halide to introduce an N-attached functionalised group or functionalised spacer group, e.g. as shown in the following reaction scheme:

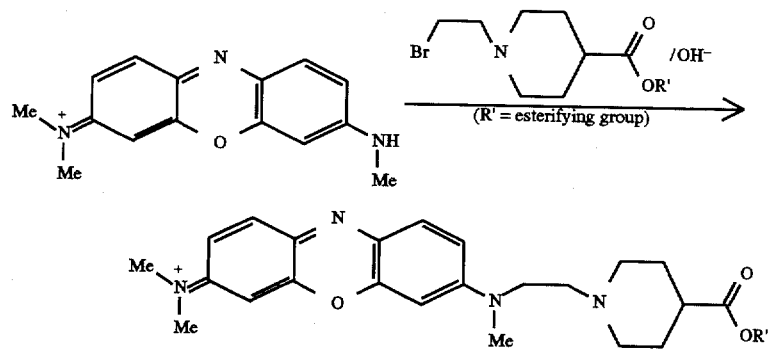

followed by hydrolysis to yield the compound in which R'=H.

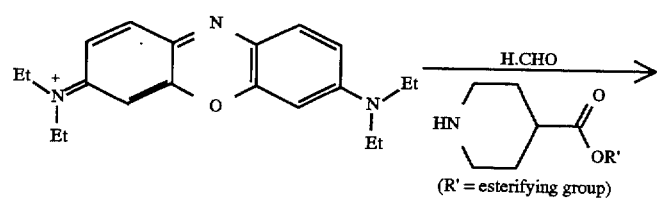

-continued

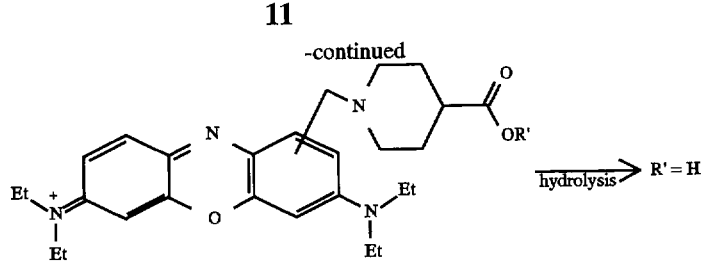 → R'=H
hydrolysis

Such carboxyl group-containing precursors may readily be reacted with, for example, m-aminophenyl boronic acid (e.g. as hereinbefore described) to yield compounds (II) containing an amide-linked phenyl boronic acid group.

2-Amino phenoxazine or phenothiazine precursors, e.g. prepared according to sequence (B) above may, for example, be diazotised and then reacted with an alkali metal thiocyanate, to yield a corresponding 2-isothiocyanato compound. This product may be reacted with a nucleophilic amine-containing molecule such as m-aminophenyl boronic acid or a functionalised spacer, e.g. as shown in either of the following reaction schemes:

followed by hydrolysis to yield the compound in which R'=H.

1- or 4- carboxy phenoxazine or phenothiazine precursors, e.g. prepared according to sequence (C), may be reacted directly with, for example, an aminophenyl boronic acid in the presence of a soluble carbodiimide or may first be modified to introduce a functionalised spacer group, e.g. as shown in the following reaction scheme:

(i)

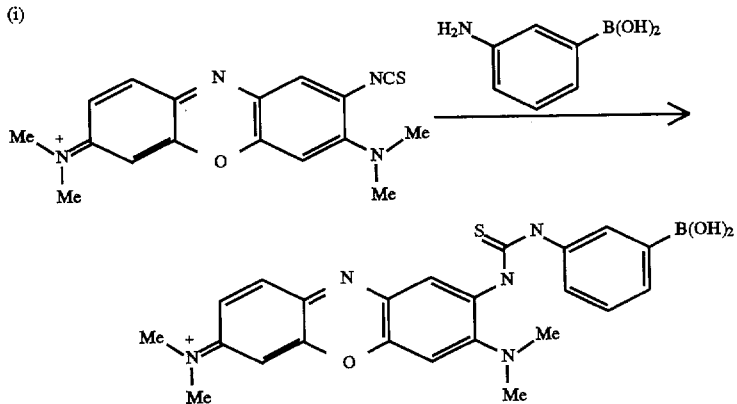

(ii)

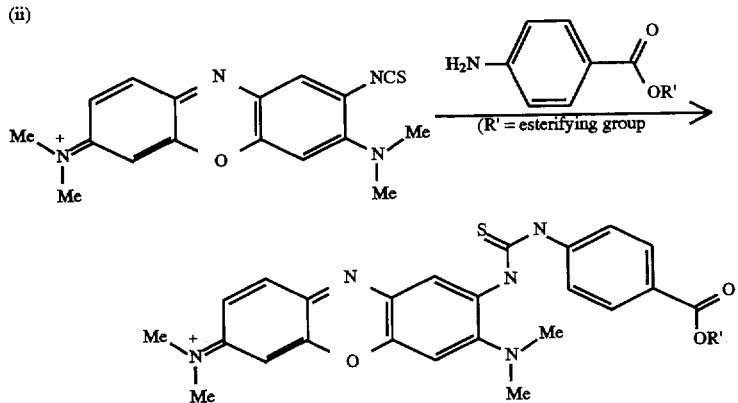

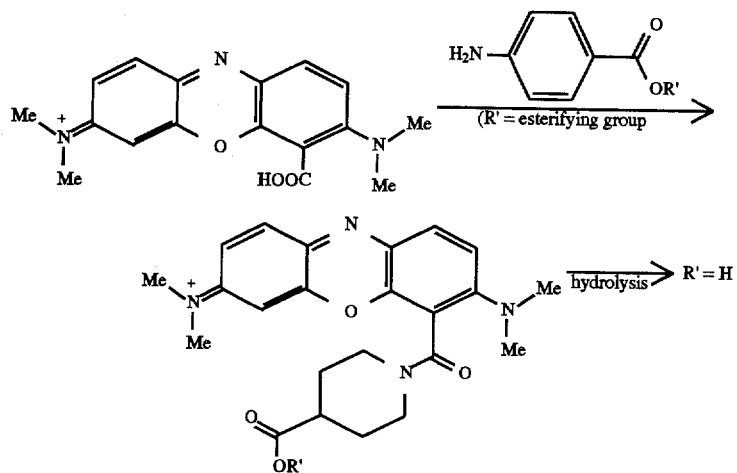

2-Acetyl phenoxazine or phenothiazine precursors, e.g. prepared according to sequence (D), may for example be subjected to a Mannich reaction to introduce an N-linked spacer group as exemplified by the following reaction scheme:

3-dimethylamino-7-dimethyliminophenothiazonium, may similarly be subjected to a Mannich reaction to ring-attach an amine group-containing functionalised group, e.g. using m-aminophenyl boronic acid as the amine as shown in the following reaction scheme:

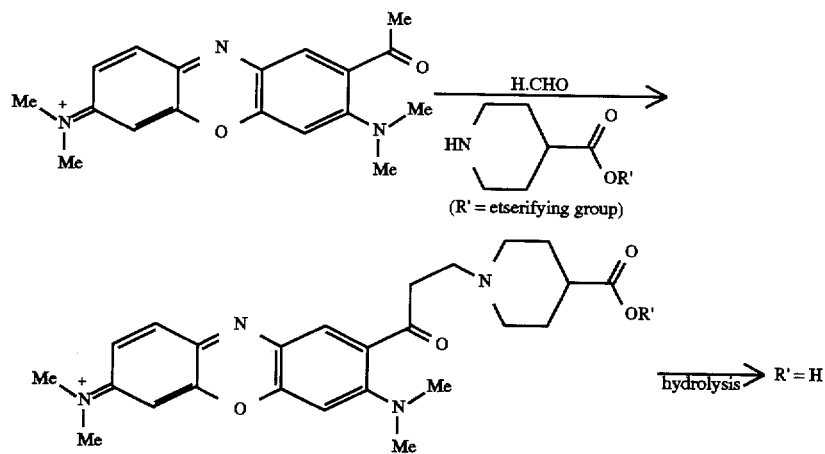

Phenoxazine and phenothiazine precursors, e.g. a conventionally prepared phenothiazine dye such as

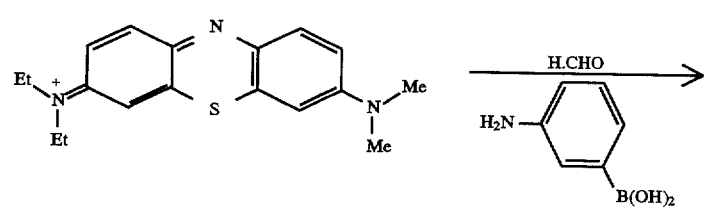

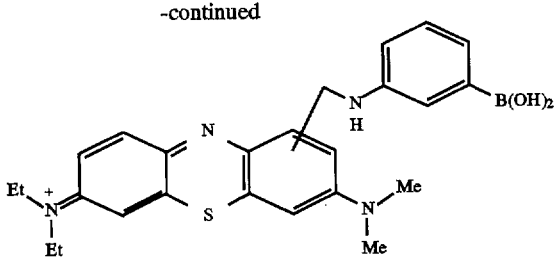

According to a further feature of the invention there are provided compounds of formula (II) as hereinbefore defined with the modification that at least one of $R_1$-$R_{10}$ is an organic group containing an activated moiety other than a boronic acid residue, said activated moiety being capable of reacting under mild chemical conditions with a target functional group in a compound to be labelled, resulting in covalent coupling of said compound (II) to said compound to be labelled, said compound (II) exhibiting an absorption maximum at not less than 600 nm.

The nature of the activated moiety present in at least one of the groups $R_1$-$R_{10}$ will, of course, depend on the nature of the target functional group to be labelled; appropriate groups may readily be selected from literature. Examples of activated derivatives with specific activity towards amine groups include, for example, N-hydroxysuccinimide active esters, imido esters, isothiocyanates and nitroarylhalides. Activated derivatives with specific reactivity towards sulf-hydryl groups include maleimides, pyridyl disulfides, thiophthalimides and active halides. Where the target functional group comprises an olefinic or aromatic carbon—carbon double bond, carbene precursors such as diazoalkanes and diazirines and nitrene precursors such as azides may provide useful active moieties.

The activated moiety may be linked to the remainder of the phenoxazine or phenothiazine (II) either directly, via a linking group (e.g. containing one or more amine or amide groups), or via a spacing moiety (e.g. as known in the art).

These compounds (II) of the present invention, by virtue of their characteristic absorption maxima at wavelengths of at least 600 nm, may be used as chromophores (and where appropriate as fluorophores) in a variety of labelling applications, especially in the presence of haemoglobin and other commonly encountered spectroscopically interfering substances. They are also useful in both single and multiple label fluorometric methods since their fluorescent emission is in the red region of the spectrum where background fluorescence is less marked. Accordingly the compounds possess useful applications as signal generating molecules in a wide range of assay techniques based on absorption, reflection and fluorescence measurements, particularly in techniques involving studies of whole blood samples. They are also useful as fluorescent probes in techniques such as fluorescence microscopy, fluoro-histochemical examination and fluorescence-activated cell sorting and analysis.

Such compounds (II) may be prepared according to the invention by reacting a precursor therefor so as to generate the desired active moiety. Thus, for example, a hydroxy group-containing precursor may be activated by treatment with a reagent such as a cyanogen halide, a triazine, a periodate, a bisoxirane, tresyl chloride or tosyl chloride. An amine group-containing precursor may, for example, be activated by diazotisation or by reaction with a bifunctional agent such as a dialdehyde. Carboxyl group-containing precursors may be activated by, for example, N-hydroxy succinimide esters, maleimides, carbodiimides or a carbonyldiimidazole, or by the mixed anhydride method.

Viewed from a further aspect the invention also provides the use of the hereinbefore defined boronic acid conjugates in a blood assay procedure, e.g. as described in the prior art mentioned above or in WO-A-90/13818.

The following non-limitative Examples serve to illustrate the invention:

EXAMPLE 1

PHENOXAZINE—BORONIC ACID CONJUGATE a) m-Formamidophenol

A mixture of 100 g m-aminophenol and 150 g formic acid was refluxed for 1.5 h and then evaporated to dryness under reduced pressure (90°–95° C., 10–15 mm Hg). Solid material was dried at 100° C., 10 mm Hg, for 1.5 h. 117 g of the title compound were isolated, melting point 112° C.

b) m-(N-methylamino)phenol

Under constant stirring 13.8 g of the product from (a) above were added in portions during 1 h to a solution of lithium aluminium hydride (9.5 g) in 180 ml dry tetrahydrofuran at 15°–20° C. The mixture was refluxed for 0.5 h, cooled to −5° C. and 385 ml 3N HCl were slowly added. The volume of the slurry was reduced to 300 ml by rotary evaporation at 60°–70° C., 400 ml water were added and again the slurry was evaporated to a final volume of 400 ml. To the remaining gray slurry were added 2 g active carbon and 10 g Celite; the resulting mixture was filtered and 60 ml 40% NaOH were added. Finally the solution was extracted twice, each time with 100 ml ether, and the extract was dried to a viscous oil and distilled. 9.3 g of the title compound, b.p. 160° C., were isolated as a viscous oil.

c) m-(N-2-ethoxycarbonylethyl-N-methylamino)phenol

A mixture of 9.3 g of the product from (b) above, 27.4 g ethyl 3-bromopropionate, 12.6 g sodium bicarbonate and 120 ml acetone was refluxed for 43 h. A new portion of 27.4 g ethyl 3-bromopropionate was then added, and the solution refluxed for a further 72 h. Finally the solution was cooled and filtered. The filtrate was evaporated to dryness (10 mm Hg, 85°–90° C.) and the residue solubilized in 50 ml CHCl$_3$:EtOAc 9:1. After chromatography on silica, using CHCl$_3$:EtOAc 9:1 as eluant, 3.8 g of the title compound were isolated.

d) 3-(N-2-Ethoxycarbonylethyl-N-methylamino)-6-(4-N,N-dimethylaminophenylimino)cyclohexa-2,4-dienone, zinc chloride adduct A mixture of 6.6 g of the product from (c) above, 4.5 g of 4-nitroso-N,N-dimethylaniline and 4.9 g zinc chloride in 88 ml methanol was refluxed for 3 h. Solid material was isolated by filtration, washed twice with 25 ml methanol and dried at 50° C., 10 mm Hg. 11.6 g of the title compound were isolated.

e) 3-Dimethylamino-7-(N-methyl-N-2-ethoxycarbonylethylimino)phenoxazonium 1.0 g of the product from (d) above was dissolved in 50 ml acetic acid, heated to 70° C. and then 180 mg NaNO$_2$ were added. The solution was kept at 70° C. under constant stirring for 6 h, then cooled, filtered and evaporated to dryness. The residue was dissolved in 40 ml H$_2$O and filtered. Finally the filtrate was evaporated to dryness at 60° C., 10 mm Hg. 0.6 g of the title compound was isolated.

f) 3-Dimethylamino-7-(N-methyl-N-2-carboxyethylimino) phenoxazonium

The product from (e) above was hydrolyzed with an equimolar amount of NaOH(aq) in 80% dioxane, and the title compound was isolated by anion exchange chromatography.

g) Conjugation to m-aminophenyl boronic acid 9.0 mg (2.29×10$^{-5}$ mol) of the product from (f) above were added to 1000 µl dry dimethylformamide and the solution was cooled to −10° C. N-methylmorpholine (2.78 mg, 2.75×10$^{-5}$ mol) and isobutyl chloroformate (3.76 mg, 2.75×10$^{-5}$ mol) were added at −10° C. and incubated on ice for 0.5 h. m-Aminophenyl boronic acid (14.2 mg, 9.17×10$^{-5}$ mol) and further N-methylmorpholine (2.78 mg, 2.75×10$^{-5}$ mol) were added and the reaction mixture was incubated for 2 h at 4° C. and 4 h at room temperature. 4 ml of the phenyl boronic acid/phenoxazine conjugate were isolated by reversed phase chromatography. The absorption maximum (λ max) of this product in the visible part of the spectrum was recorded at 642 nm, with a molar extinction coefficient (ε) of >70,000 1/mol.cm.

EXAMPLE 2

TRIPHENYLMETHANE DYE—BORONIC ACID CONJUGATE a) Xylene cyanole, which may be represented by the formula

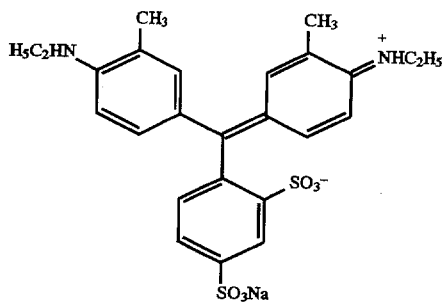

(75 mg, 80% pure, 1.11×10$^{-4}$ mol) was dried overnight at 100° C. Phosphorus oxychloride (205 µl, 2.24×10$^{-3}$ mol) was added and the mixture was incubated at room temperature under exclusion of moisture. After 24 hours at this temperature, the mixture was washed several times with dry n-hexane to extract an unwanted yellow reaction by-product and unreacted phosphorus oxychloride. When the hexane extract was free of colour, chloroform was added to extract the xylene cyanole sulphonyl chloride. Finally, the chloroform extract (15 ml) was washed five times with 1 ml portions of cold water and then evaporated to dryness under reduced pressure and exclusion of moisture.

The solid material was immediately solubilised in 200 µl N,N-dimethylformamide (DMF), to which solution 3-aminophenyl boronic acid monohydrate (17 mg, 1.10× 10$^{-4}$ mol) in 100 µl DMF was added. The mixture was allowed to stand for 5 minutes, whereafter 2 ml of a 0.75M sodium carbonate/sodium bicarbonate buffer (pH 10.0) was added under constant stirring, and the solution incubated at room temperature for 3–12 hours. The pH of the solution was monitored and kept between 8 and 9.5.

The boronic acid conjugates were isolated by reversed phase chromatography, mainly in the form of mono(phenyl boronic acid)-functionalised dye, λ max 619 nm (ε>70,000).

b) The procedure of part (a) of this Example was repeated, except that 2-nitro-5-aminophenyl boronic acid monohydrate (22 mg, 1.1×10$^{-4}$ mol) was employed in place of the 3-aminophenyl boronic acid, giving mainly a mono(phenyl boronic acid)-functionalised dye with similar spectroscopic properties to the product of part (a).

EXAMPLE 3

PHTHALOCYANINE DYE—BORONIC ACID CONJUGATE

Chloroaluminium phthalocyanine tetrasulphonate (100 mg, 1.12×10$^{-4}$ mol) was dried overnight at 100° C. Phosphorus oxychloride (410 µl, 4.48×10$^{-3}$ mol) was added and the mixture was incubated at room temperature under exclusion of moisture. After 24 hours at this temperature, the solid material was washed several times with a total of 10 ml n-hexane to remove unreacted phosphorus oxychloride.

The remaining solid phthalocyanine sulphonyl chloride was dried under reduced pressure and exclusion of moisture, and then immediately solubilised in DMF (500 µl). To this solution was added 3-aminophenyl boronic acid monohydrate (20 mg, 1.20×10$^{-4}$ mol) in DMF (100 µl). The mixture was allowed to stand for 5 minutes, whereafter 2 ml of a 0.75M sodium carbonate/sodium bicarbonate buffer (pH 10.0) were added. The reaction mixture was incubated at room temperature under constant stirring for 3–12 hours, during which time the pH of the solution was monitored and kept between 8 and 9.5. The boronic acid conjugates were isolated by reversed phase chromatography, mainly in the form of mono(phenyl boronic acid)-functionalised dye, λ max 676 nm (ε=160,000).

EXAMPLE 4

CYANINE DYE—BORONIC ACID CONJUGATE

Phosphorus oxychloride (470 µl, 5.13×10$^{-3}$ mol) was added to the cyanine dye 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e] indolium hydroxide, inner salt, sodium salt (commercially known as IR 125 or indocyanine green) (100 mg, 1.29×10$^{-4}$ mol) and the resulting mixture was incubated at room temperature under exclusion of moisture for 24 hours. The dark brown solution was then poured over crushed ice and left for 5 minutes. The IR-125 sulphonyl chloride was extracted into chloroform, and the extract was washed five times with 1 ml portions of cold water and then evaporated to dryness under reduced pressure and exclusion of moisture.

The resulting solid material was immediately solubilised in DMF (500 µl), to which solution was added 3-aminophenyl boronic acid monohydrate (17 mg, 1.10× 10$^{-4}$ mol) in DMF (100 µl). The mixture was allowed to stand for 5 minutes, whereafter 2 ml of a 0.75M sodium carbonate/sodium bicarbonate buffer (pH 10.0) were added under constant stirring and the solution was incubated at room temperature for 3–12 hours, during which time the pH of the solution was monitored and kept between 8 and 9.5. The boronic acid conjugates were isolated by reversed phase chromatography, mainly in the form of mono(phenyl boronic acid)-functionalised dye, λ max 799 nm (ε≈200,000).

EXAMPLE 5

CYANINE DYE—BORONIC ACID CONJUGATE

To the reactive succinimidyl ester-cyanine dye Cy5.18 (1.3×10$^{-7}$ mol) were added 2 mg 3-aminophenyl boronic acid in 0.5 ml 0.1M sodium carbonate/sodium bicarbonate buffer (pH 9.3), with subsequent thorough mixing. The mixture was incubated under constant stirring at room temperature for 4 h, and the phenyl boronic acid conjugate finally isolated by reversed phase chromatography, λ max 652 nm (ε≈200,000).

EXAMPLE 6

MEASUREMENT OF GLYCOSYLATED HAEMOGLOBIN IN WHOLE BLOOD USING PHTHALOCYANINE DYE—BORONIC ACID CONJUGATE

A sample of whole blood was mixed with a haemolysing reaction buffer (pH 9.4) containing 160 mM piperazine, 0.07% Triton X-100, 9.4% ethanol (v/v), 9.4% butanol (v/v) and phthalocyanine-boronic acid conjugate prepared as described in Example 3, at a final concentration of $2.1\times10^{-5}$M. The final haemoglobin concentration was approximately 2 mg/ml. The whole blood was haemolysed, and a precipitate was formed. The precipitated haemoglobin was separated by filtration, and its reflectance measured at 685 and 470 nm by means of a Schimadzu Dual Wavelength Flying Spot Scanner CS 9000. The ratio of the reflectances at 685 and 470 nm was calculated, and the percentage of glycosylated haemoglobin to total haemoglobin was determined from a calibration curve obtained using standard solutions of known concentrations of haemoglobin and glycosylated haemoglobin.

EXAMPLE 7

MEASUREMENT OF GLYCOSYLATED HAEMOGLOBIN IN WHOLE BLOOD USING XYLENE CYANOLE—BORONIC ACID CONJUGATE

The procedure of Example 6 was repeated except that xylene cyanole-boronic acid conjugate prepared as described in Example 2 was used, at a concentration of $2.1\times10^{-5}$M, in place of the phthalocyanine dye conjugate and that reflectances were measured at 635 and 470 nm.

We claim:

1. A non-proteinaceous boronic acid conjugate compound having an absorption maximum at not less than 600 nm and having the formula $$V\text{—}W\text{—}B(OH)_2 \qquad (I)$$

wherein V is a triphenylmethane moiety exhibiting an absorption maximum at not less than 600 nm, and W is a linking organic group.

2. Compounds as claimed in claim 1 wherein the boron atom is attached to an aminophenyl group in which the phenyl ring is optionally further substituted by one or more substituents selected from nitro, lower alkoxy and formyl groups.

3. Compounds as claimed in claim 2 wherein the boron atom is attached to a m-aminophenyl group.

4. A process for the preparation of a boronic acid conjugate as defined in claim 1 which comprises reacting an appropriately functionalised dye having an absorption maximum of not less than 600 nm with one or more reagents serving to introduce a boronic acid residue.

5. A method of assaying blood comprising adding to a blood sample a compound according to claim 1, and measuring resulting absorption, reflection and/or fluorescence.

* * * * *